(12) United States Patent
Song et al.

(10) Patent No.: US 11,129,625 B2
(45) Date of Patent: Sep. 28, 2021

(54) PATIENT-CUSTOMIZED SURGICAL INSTRUMENT FOR TIBIA AND SURGICAL MODULE USING SAME

(71) Applicant: CORENTEC CO., LTD, Cheonan-si (KR)

(72) Inventors: Eun-Kyoo Song, Gwangju (KR); Jong-Keun Seon, Gwangju (KR); Jung-Sung Kim, Seoul (KR); Jun-Kyu Park, Cheonan-si (KR); Jae-Won Kim, Cheonan-si (KR)

(73) Assignee: Corentec Co., Ltd, Cheonan-si (KR)

( * ) Notice: Subject to any disclaimer, the term of this patent is extended or adjusted under 35 U.S.C. 154(b) by 542 days.

(21) Appl. No.: 15/101,141

(22) PCT Filed: Oct. 23, 2014

(86) PCT No.: PCT/KR2014/010013
§ 371 (c)(1),
(2) Date: Jun. 2, 2016

(87) PCT Pub. No.: WO2015/099275
PCT Pub. Date: Jul. 2, 2015

(65) Prior Publication Data
US 2016/0302800 A1  Oct. 20, 2016

(30) Foreign Application Priority Data
Dec. 24, 2013 (KR) .................. 10-2013-0162144

(51) Int. Cl.
*A61B 17/15* (2006.01)
*A61B 17/16* (2006.01)
*A61B 17/17* (2006.01)
*A61B 17/56* (2006.01)

(52) U.S. Cl.
CPC ........ *A61B 17/157* (2013.01); *A61B 17/1604* (2013.01); *A61B 17/1659* (2013.01);
(Continued)

(58) Field of Classification Search
CPC .............. A61B 17/157; A61B 17/1764; A61B 17/1659; A61B 17/1675; A61B 17/1604; A61B 2017/568
See application file for complete search history.

(56) References Cited

U.S. PATENT DOCUMENTS 5,356,414 A   10/1994  Cohen et al.
5,976,147 A * 11/1999  LaSalle .............. A61B 17/1604
                                                  606/102
(Continued)

FOREIGN PATENT DOCUMENTS

KR   10-2006-0015966 A    2/2006
KR      10-0925282 B1    11/2009

OTHER PUBLICATIONS

International Search Report dated Feb. 16, 2015, issued in PCT application No. PCT/KR2014/010013, filed Oct. 23, 2014.
(Continued)

*Primary Examiner* — Kevin T Truong
*Assistant Examiner* — Tracy L Kamikawa
(74) *Attorney, Agent, or Firm* — Workman Nydegger

(57) ABSTRACT

A patient-customized surgical instrument used to form a surgical site in a tibia for implantation of an implant into the tibia, and a surgical module using the same. A body part is coupled to the tibia to surround a portion of the tibia. A cutting-member insertion window is formed through a side of the body part to receive a cutting member that is inserted to form a cutting plane of the tibia. A position setting hole is formed through the upper side of the body part to receive and guide a post recess forming member that is used to form a post recess in the tibia. A post of the tibia element is received in the post recess. A surgical site can be accurately and easily formed in a damaged tibia.

17 Claims, 7 Drawing Sheets

(52) U.S. Cl.
CPC ...... *A61B 17/1675* (2013.01); *A61B 17/1764* (2013.01); *A61B 2017/568* (2013.01)

(56) References Cited

U.S. PATENT DOCUMENTS

| | | | | |
|---|---|---|---|---|
| 6,228,091 | B1 | 5/2001 | Lombardo | |
| 6,620,168 | B1* | 9/2003 | Lombardo | A61B 17/1735 606/102 |
| 7,390,327 | B2* | 6/2008 | Collazo | A61B 17/1675 606/88 |
| 8,122,582 | B2* | 2/2012 | Burdulis, Jr. | A61B 17/155 29/527.1 |
| 2012/0209394 | A1* | 8/2012 | Bojarski | A61F 2/30942 623/20.32 |
| 2012/0310399 | A1 | 12/2012 | Metzger | |
| 2012/0316564 | A1* | 12/2012 | Serbousek | A61B 17/1764 606/80 |
| 2013/0296874 | A1* | 11/2013 | Chao | A61B 17/157 606/88 |
| 2013/0317510 | A1* | 11/2013 | Couture | A61B 17/157 606/88 |
| 2014/0114319 | A1* | 4/2014 | Wilkinson | A61B 34/10 606/88 |

OTHER PUBLICATIONS

Written Opinion dated Feb. 16, 2015, issued in PCT application No. PCT/KR2014/010013, filed Oct. 23, 2014.

* cited by examiner

PATIENT-CUSTOMIZED SURGICAL INSTRUMENT FOR TIBIA AND SURGICAL MODULE USING SAME

TECHNICAL FIELD

The present invention generally relates to a patient-customized surgical instrument used in the formation of a surgical site on a tibia such that a tibial element is able to be transplanted on the tibia, and a surgical module using the same. More particularly, the present invention relates to a patient-customized tibial surgical instrument and a surgical module using the same, the patient-customized surgical instrument comprising: a body coupled to a tibia and surrounding a portion of the tibia; a cutting member insertion window extending through a portion of the body and accommodating a cutting member inserted thereinto to form an amputation plane of the tibia; and a positioning hole extending through a top part of the body, wherein the positioning hole accommodates and guides a post recess-forming member used to form a post recess in the tibia, the post recess accommodating a post of the tibial element, such that the surgical site can be formed accurately and easily on the damaged tibia.

BACKGROUND ART

When a knee joint malfunctions due to arthritis, an external wound, or the like, arthroplasty is performed by transplanting an implant able to substitute for the damaged joint, such that an artificial joint performs the function of a normal knee joint.

FIGS. 1 to 3 are reference views illustrating arthroplasty performed on a knee joint. With reference to FIGS. 1 to 3 and the following patent document, an arthroplasty method of the related art will be described.

RELATED ART DOCUMENT

Korean Patent No. 10-1190973 (Oct. 8, 2012): "APPARATUS AND METHOD FOR DISPLAYING AMPUTATION PLANE OF KNEE JOINT"

FIG. 1 illustrates a knee joint in which arthroplasty has been performed. A femoral element 300 is coupled to a femur 100, and a tibial element 400 is coupled to a tibia 200. A bearing 500 is positioned between the femoral element 300 and the tibial element 400. In order to transplant the femoral element 300 and the tibial element 400 illustrated in FIGS. 1 and 2 to the femur 100 and the tibia 200, surgical sites must be formed on the femur 100 and the tibia 200 as illustrated in FIG. 3. Amputation planes 120a and 220 are formed on the surgical sites using a stereotyped cutting block disclosed in the patent document or the like. The amputation planes 120a and 220 are formed by abutting the cutting block to the femur 100 or the tibia 200 and then inserting a cutting instrument through a slit.

However, the bone structure and shape of every patient are unique. When the stereotyped cutting block is used, it is impossible to set accurate positions of the amputation planes 120a and 220. Therefore, a patient-customized cutting block is used. In this regard, a three-dimensional (3D) image of a cutting block conforming to the 3D image of the femur 100 or the tibia 200 is formed by capturing an image of the femur 100 or the tibia 200 of a patient and then converting the captured image into a 3D image. Afterwards, the patient-customized cutting block is fabricated on the basis of the 3D image of the cutting block.

In addition, after the amputation plane 220 is formed on the tibia 200 using the cutting blocks, the cutting blocks are removed, and a seating recess 230 accommodating a post 420 and keels 430 of the tibial element 400 is formed. A post recess 231 accommodating the post 410 of the tibial element 400 is formed in the tibia 200 using a drill, and then keel recesses 232 accommodating the keels 430 of the tibial element 400 are formed. However, since the process of forming the seating recess 230 in the tibia 200 is complicated, errors in surgery increase or operation time and costs may increase, which is problematic.

DISCLOSURE

Technical Problem

Accordingly, the present invention has been made keeping in mind the above problems occurring in the related art.

The present invention is intended to propose a patient-customized tibial surgical instrument and a surgical module using the same, the patient-customized surgical instrument being able to simplify the process of forming a surgical site on a tibia to reduce errors in a surgery and reduce surgery time and costs.

In addition, the present invention is intended to propose a patient-customized tibial surgical instrument and a surgical module using the same, the patient-customized surgical instrument having a positioning hole formed in a portion of a body that is to be coupled to the tibia, on the basis of three-dimensional (3D) data of the tibia, to guide a post recess-forming member, such that a post recess can be accurately and easily formed in the surgical site since it is not required to determine the position in which the post recess is to be formed.

Furthermore, the present invention is intended to propose a patient-customized tibial surgical instrument and a surgical module using the same, the patient-customized surgical instrument including a keel recess-forming member, the distal end of which is pressed to form the keel recess after the keel recess-forming member is coupled to an amputation plane formed in the post recess, such that the keel recess can be accurately and easily formed.

In addition, the present invention is intended to propose a patient-customized tibial surgical instrument and a surgical module using the same, the patient-customized surgical instrument including a mechanical axis indicator disposed on a portion of the body that is to be coupled to a tibia, the mechanical axis indicator allowing the mechanical axis of the tibia to be visually identified, such that the patient-customized tibial surgical instrument fabricated on the basis of the 3D data of the tibia can be placed in position on the damaged tibia, thereby accurately and easily forming the amputation plane of the tibia.

Furthermore, the present invention is intended to propose a patient-customized tibial surgical instrument and a surgical module using the same, in which an amputation plane guideline formed on the basis of the 3D data of the tibia guides the position of a cutting member, whereby the amputation plane can be accurately formed.

Technical Solution

In order to achieve the above object, the present invention is realized by embodiments having the following features.

According to an embodiment of the present invention, provided is a patient-customized tibial surgical instrument used in formation of a surgical site such that a tibial element is able to be transplanted on a tibia. The patient-customized tibial surgical instrument may include: a body coupled to a tibia and surrounding a portion of the tibia; a cutting member insertion window extending through a portion of the body and accommodating a cutting member inserted thereinto to form an amputation plane of the tibia; and a positioning hole extending through a top part of the body, wherein the positioning hole accommodates and guides a post recess-forming member used to form a post recess in the tibia, the post recess accommodating a post of the tibial element.

According to another embodiment of the present invention, the positioning hole may be formed on basis of three-dimensional (3D) data of the tibia.

According to further another embodiment of the present invention, the patient-customized tibial surgical instrument may further include a mechanical axis indicator disposed on the body to provide an indication with which a mechanical axis of the tibia is visually identifiable. The mechanical axis indicator includes: a connector protruding from a front portion of the body to fix an indicator bar to the body; and the indicator bar coupled to the connector to be fixed to the body and allowing a position of the mechanical axis to be identified. When one end of the indicator bar is directed to an intercondylar eminence of a tibial plateau and the other end of the indicator bar is directed to a talocrural joint, the indicator bar is aligned with the mechanical axis of the tibia.

According to still another embodiment of the present invention, the patient-customized tibial surgical instrument may further include an amputation plane guideline disposed on a portion of the body to provide an indication with which a position of the amputation plane to be formed on the tibia is identifiable.

According to another embodiment of the present invention, provided is a surgical module using a patient-customized tibial surgical instrument used in formation of a surgical site such that a tibial element is able to be transplanted on a tibia. The surgical module may include: a patient-customized tibial surgical instrument coupled with a proximal end of a tibia to be used in formation of an amputation plane and a post recess of a surgical site; and a keel recess-forming member. After the amputation plane and the post recess of the surgical site are formed using the patient-customized tibial surgical instrument, the keel recess-forming member is coupled to the amputation plane to form a keel recess. The patient-customized tibial surgical instrument includes the patient-customized tibial surgical instrument as described above.

According to further another embodiment of the present invention, the keel recess-forming member may include: a casing having one end inserted into the post recess to accommodate a keel recess-forming part that is movable up and down; a support plate coupled to an outer periphery of the casing to abut the amputation plane of the tibia; and the keel recess-forming part including a lift bar positioned within the casing to be movable up and down and a blade disposed on a lower periphery of the lift bar to protrude outside of the casing through a blade hole, wherein the blade is movable up and down along with the lift bar to form the keel recess in the tibia.

According to still another embodiment of the present invention, the support plate may have a guide hole extending therethrough in a top-bottom direction, the guide hole functions as a passage through which the blade moves up and down.

According to yet another embodiment of the present invention, a stopper head may be disposed on a top end of the lift bar to limit a depth to which the lift bar moves downwards.

Advantageous Effects

According to the above-described embodiments and the following features, combinations, and relations of use that will be described later, the present invention can obtain the following effects.

According to the present invention, it is possible to simplify the process of forming a surgical site on a tibia to reduce errors in a surgery and reduce surgery time and costs.

In addition, according to the present invention, it is possible to form the positioning hole in a portion of a body that is to be coupled to a tibia, on the basis of 3D data of the tibia, to guide a post recess-forming member, such that a post recess can be accurately and easily formed in the surgical site since it is not required to determine the position in which the post recess is to be formed.

Furthermore, according to the present invention, it is possible to provide the keel recess-forming member, the distal end of which is pressed to form the keel recess after the keel recess-forming member is coupled to an amputation plane formed in the post recess, such that the keel recess can be accurately and easily formed.

In addition, according to the present invention, it is possible to provide the mechanical axis indicator disposed on a portion of the body that is to be coupled to a tibia, the mechanical axis indicator allowing the mechanical axis of the tibia to be visually identified, such that the patient-customized tibial surgical instrument fabricated on the basis of the 3D data of the tibia can be placed in position on the damaged tibia, thereby accurately and easily forming the amputation plane of the tibia.

Furthermore, according to the present invention, the amputation plane guideline formed on the basis of the 3D data of the tibia guides the position of a cutting member, whereby the amputation plane can be accurately formed

BEST MODE

Reference will now be made in greater detail to a surgical module using a patient-customized tibial surgical instrument according to the present invention in conjunction with the accompanying drawings. Unless not specifically defined, all terminologies in the specification should be interpreted based on the general meanings thereof that a person skilled in the art understands. When the general meanings of the terminologies are incompliant with those used in the specification, the terminologies should be interpreted as being defined herein. In addition, detailed descriptions of known functions and components incorporated herein will be omitted to avoid making the subject matter of the present invention unclear.

Figure 1:
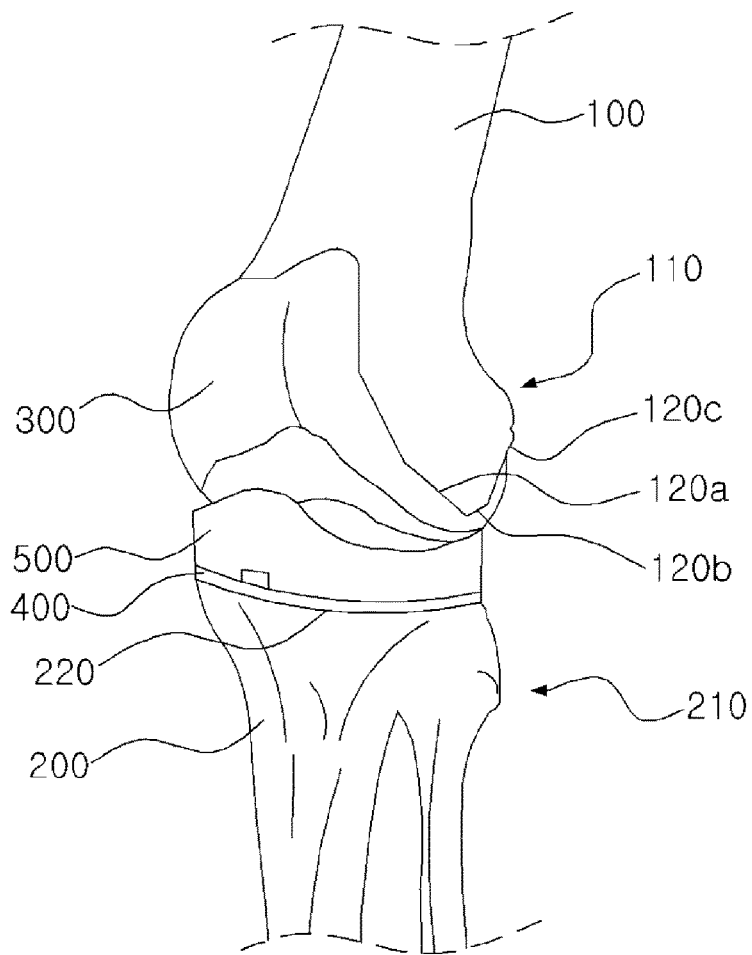
FIGS. 1 to 3 are reference views illustrating arthroplasty performed on a knee joint.
Figure 2:
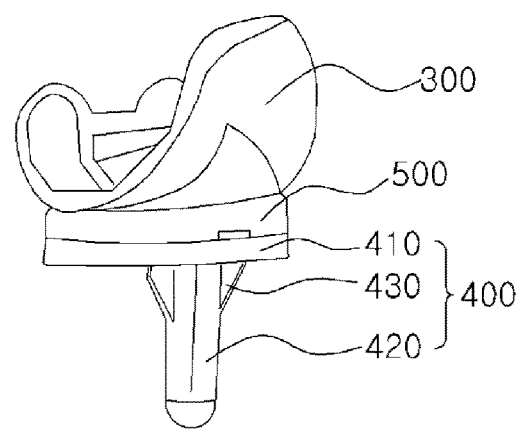
Figure 3:
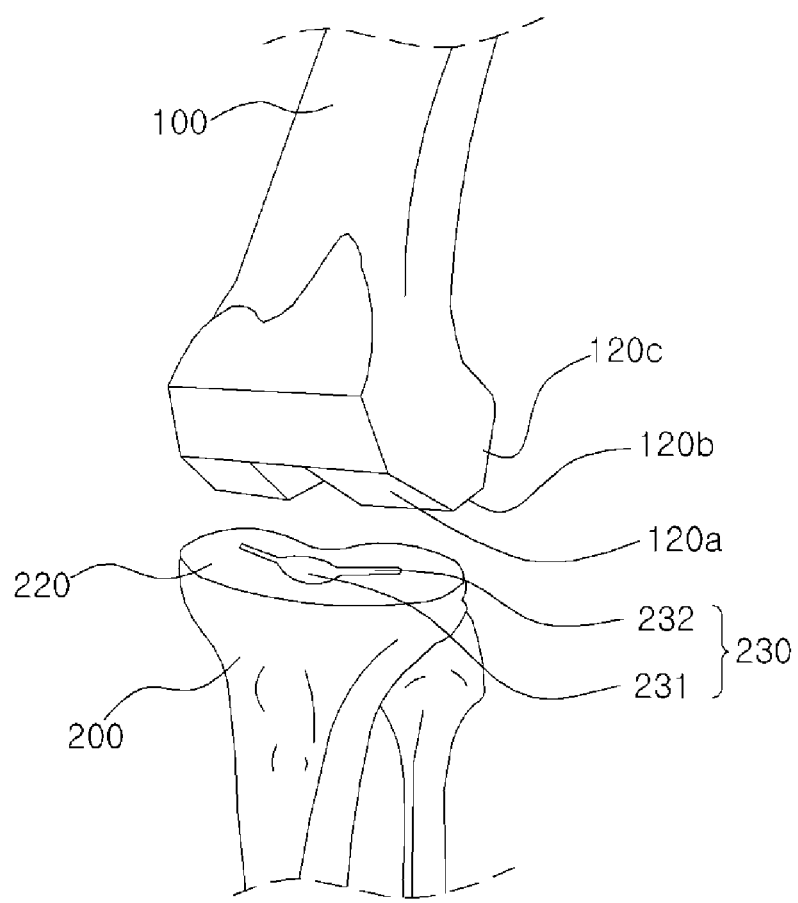
Figure 4:
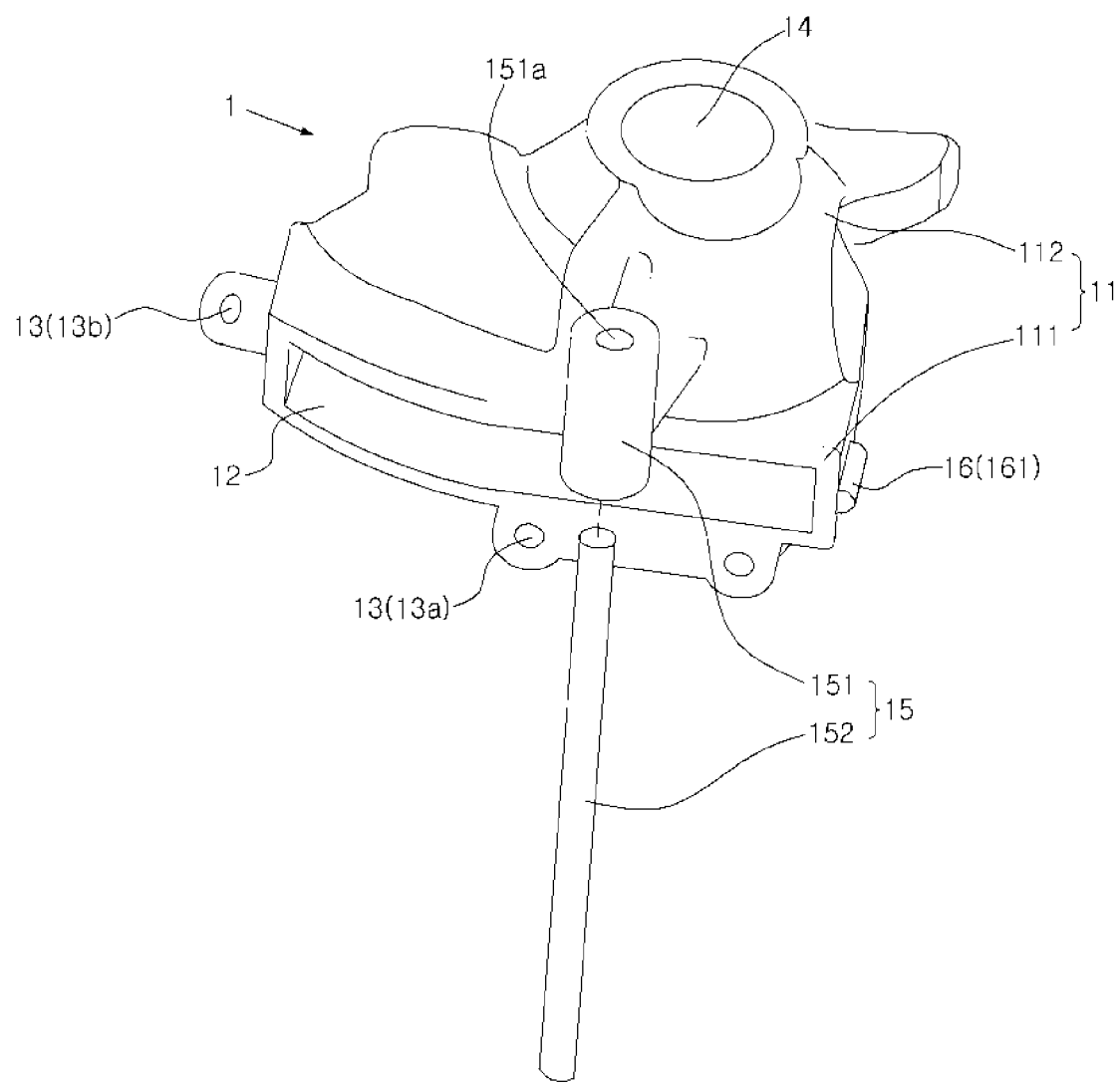
FIG. 4 is a front perspective view illustrating a patient-customized tibial surgical instrument used in a surgical module according to an embodiment of the present invention.
Figure 5:
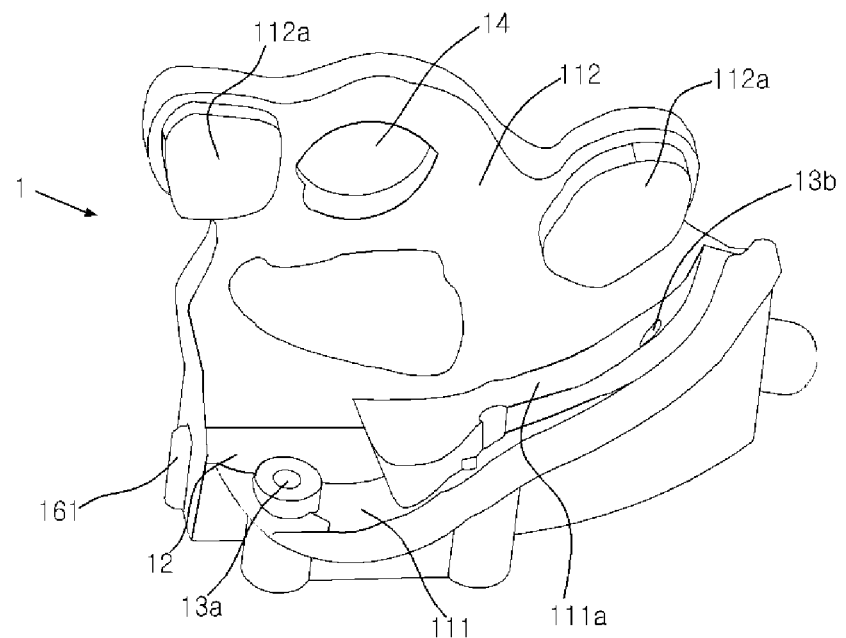
FIG. 5 is a rear perspective view of the patient-customized tibial surgical instrument illustrated in FIG. 4.
Figure 6:
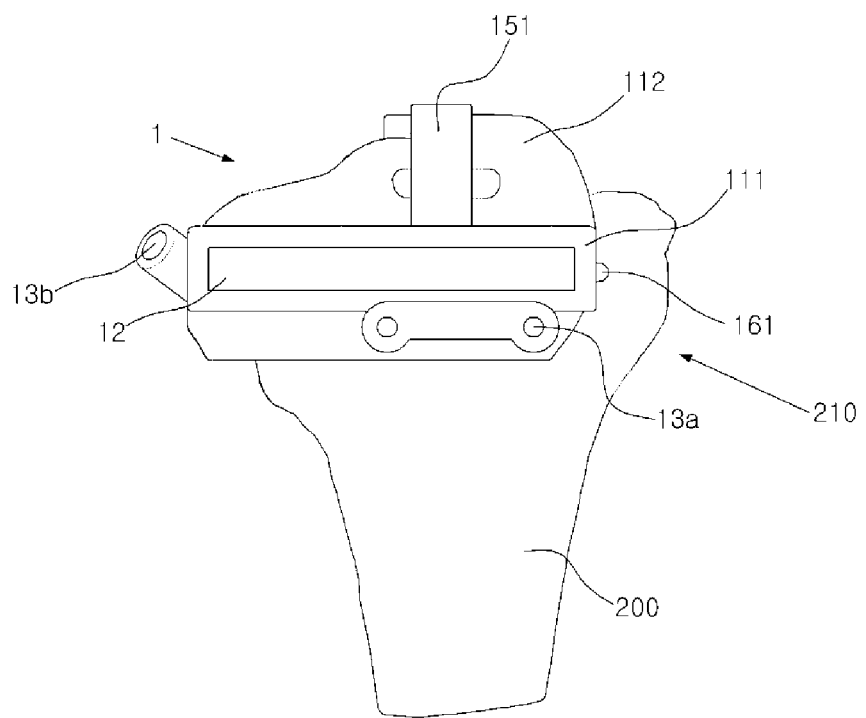
FIG. 6 is a reference view illustrating a position in which the patient-customized tibial surgical instrument illustrated in FIG. 4 is coupled with a tibia.
Figure 7:
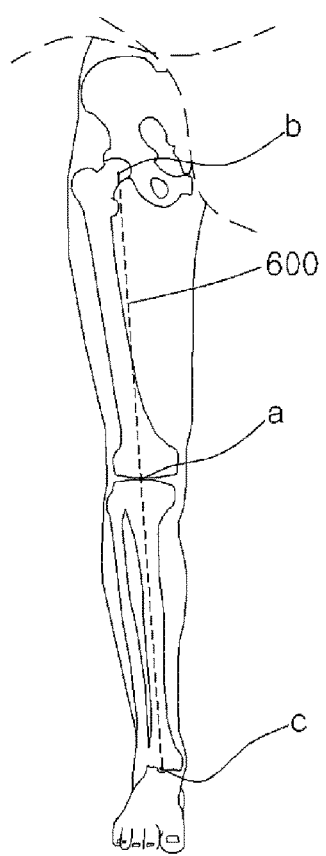
FIG. 7 is a reference view illustrating a mechanical axis of a lower limb.
Figure 8:
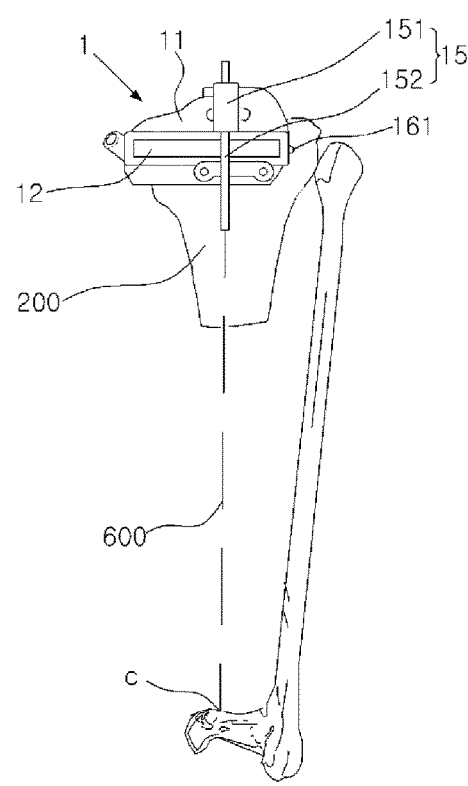
FIG. 8 is a reference view illustrating a method of identifying the mechanical axis using the patient-customized tibial surgical instrument illustrated in FIG. 4.
Figure 9:
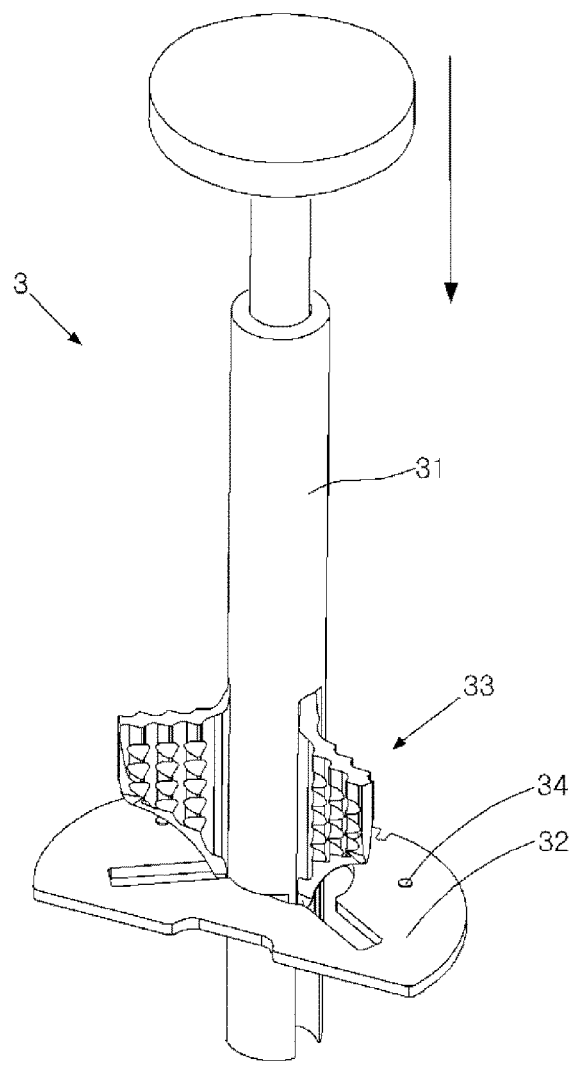
FIG. 9 is a perspective view illustrating a keel recess-forming member used in a surgical module according to an embodiment of the present invention.
Figure 10:
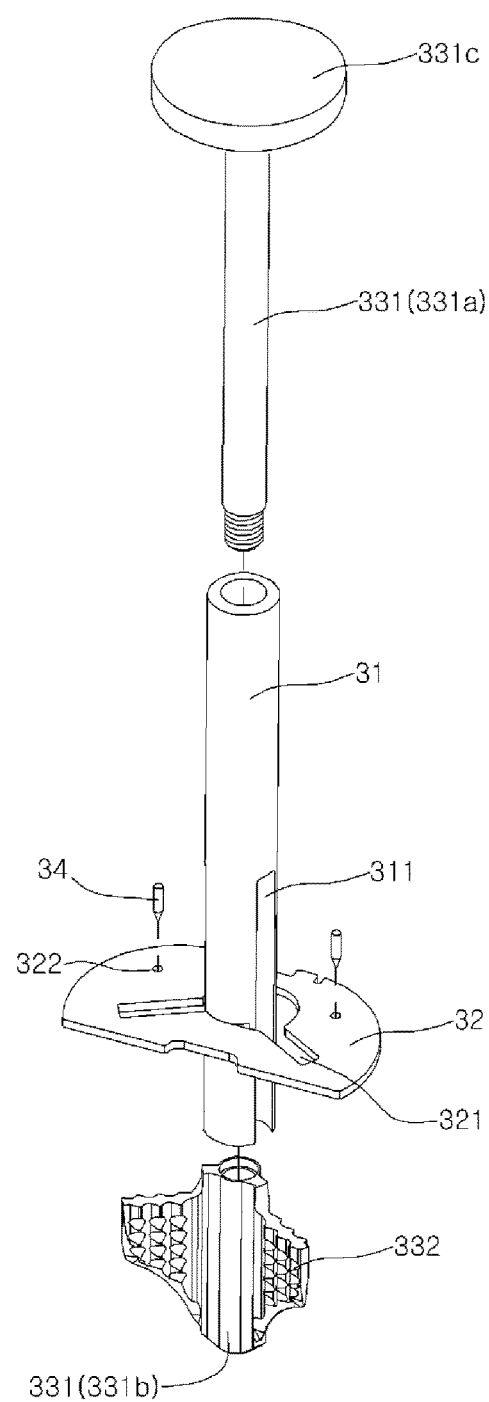
FIG. 10 is an exploded perspective view of the keel recess-forming member illustrated in FIG. 9.
Figure 11:
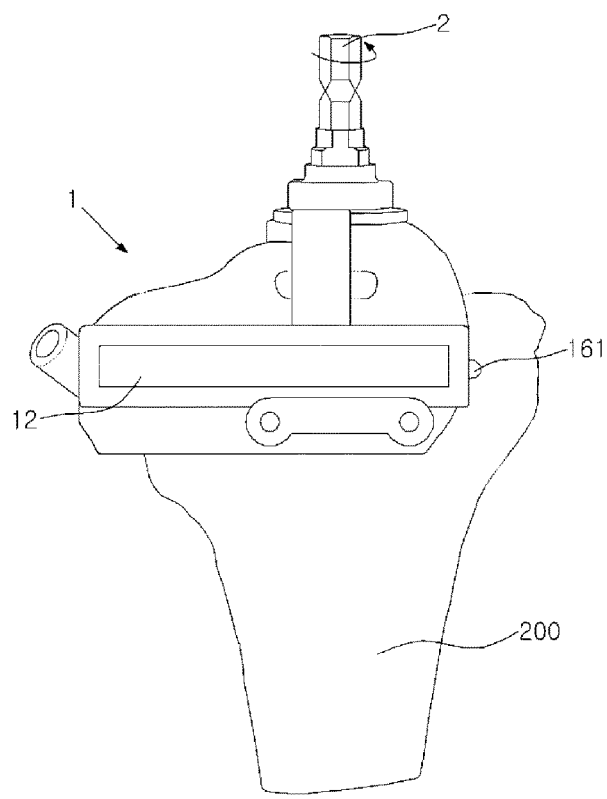
FIGS. 11 and 12 are reference views illustrating a method of forming a surgical site using the surgical module according to the embodiment of the present invention.
Figure 12:
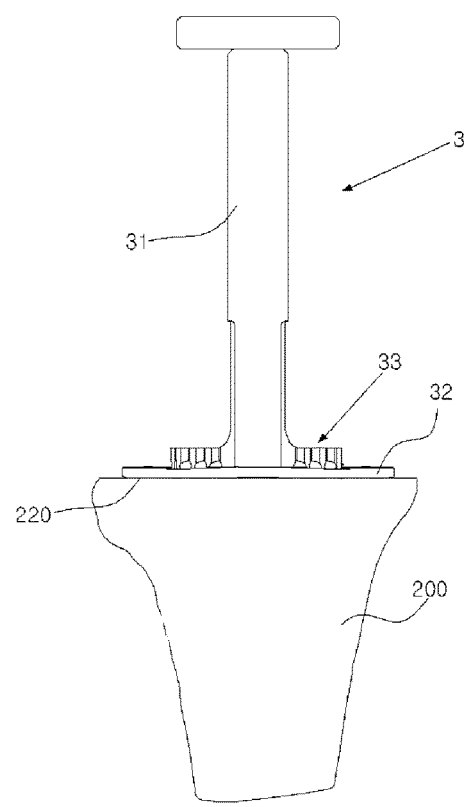

FIGS. 1 to 3 are reference views illustrating arthroplasty performed on a knee joint, FIG. 4 is a front perspective view illustrating a patient-customized tibial surgical instrument used in a surgical module according to an embodiment of the present invention, FIG. 5 is a rear perspective view illustrating the patient-customized tibial surgical instrument illustrated in FIG. 4, FIG. 6 is a reference view illustrating a position in which the patient-customized tibial surgical instrument illustrated in FIG. 4 (except for an indicator bar) is coupled with a tibia, FIG. 7 is a reference view illustrating a mechanical axis of a lower limb, FIG. 8 is a reference view illustrating a method of identifying the mechanical axis using the patient-customized tibial surgical instrument illustrated in FIG. 4, FIG. 9 is a perspective view illustrating a keel recess-forming member used in a surgical module according to an embodiment of the present invention, FIG. 10 is an exploded perspective view of the keel recess-forming member illustrated in FIG. 9, and FIGS. 11 and 12 are reference views illustrating a method of forming a surgical site using the surgical module according to the embodiment of the present invention.

A surgical module using the patient-customized tibial surgical instrument according to the embodiment of the present invention is used when forming a surgical site on the tibia 200 such that an implant (the tibial element 400) can be transplanted on the tibia 200. Hereinafter, the surgical module using the patient-customized tibial surgical instrument will be described with reference to FIGS. 1 to 12. The surgical module includes the patient-customized tibial surgical instrument 1 and a keel recess-forming member 3. The patient-customized tibial surgical instrument 1 is coupled to the proximal end 210 of the tibia 200 to be used when forming the amputation plane 220 and the post recess 231. After the amputation plane 220 and the post recess 231 of the surgical site are formed due to the use of the patient-customized tibial surgical instrument 1, the keel recess-forming member 3 is coupled to the amputation plane 220 to be used in forming the keel recesses 232 in the surgical site. The formation of the surgical site refers to processing the tibia 200 such that an implant can be transplanted. FIG. 3 illustrates the shape of the tibia 200 on which the surgical site is formed. The surgical site includes the amputation plane 220 on which a flat end 410 of the tibial element 400 is seated and the seating recess 230 accommodating the post 420 and the keels 430 protruding from the bottom of flat end 410. The seating recess 230 includes the post recess 231 accommodating the post 420 and the keel recesses 232 accommodating the keels 430. The patient-customized surgical instrument refers to a surgical instrument customized to a corresponding patient. The patient-customized surgical instrument is fabricated by acquiring computerized tomography (CT) data about a damaged tibia on which a surgical site is to be formed by performing CT scanning the CT, designing a three-dimensional (3D) image of the tibia on the basis of the CT data (using, for example, a 3D design program), extracting factors used in formation of the surgical site (e.g. a mechanical axis, an amputation plane, a seating recess, and the like) from the 3D image of the tibia, designing a 3D image of the surgical instrument to be attached to the tibia on the basis of the 3D image of the tibia and the extracted factors (hereinafter, referred to as the "3D data of the bone"), and printing the 3D image of the surgical instrument using a 3D printer. Since the patient-customized surgical instrument is individually fabricated for each patient, the patient-customized tibial surgical instrument that will abut the damaged tibia has abutting surfaces 111a and 112a configured to surround the tibia, i.e. having negative shapes of the abutting portions of the tibia, formed on the inner surface thereof. The components of the patient-customized surgical instrument, such as the abutting surfaces 111a and 112a, a cutting member insertion window 12, a positioning hole 14, a mechanical axis indicator 15, and an amputation plane guideline 161, are fabricated on the basis of the 3D data of the tibia such that the shapes and positions thereof are optimized to the patient. That is, when the patient-customized surgical instrument is placed in a set position with respect to the tibia 200, an indicator bar 152 of the mechanical axis indicator 15 is aligned with a mechanical axis 600 of the tibia 200, and the post recess 231 and the amputation plane 220 can be accurately formed, as intended, on the basis of the positioning hole 14 and the amputation plane guideline 161. This will be described later in detail. In addition, although the patient-customized surgical instrument may be formed of a variety of materials, it is preferable that the patient-customized surgical instrument is formed of a synthetic resin, such as polyethylene.

The patient-customized tibial surgical instrument 1 is a component to be used in a surgery of transplanting the tibial element 400 in which the patient-customized tibial surgical instrument 1 is coupled to the proximal end 210 of the tibia 200. The patient-customized tibial surgical instrument 1 includes a body 11, the cutting member insertion window 12, fixing holes 13, the positioning hole 14, the mechanical axis indicator 15, an indicator 16, and the like.

The body 11 is a component coupled to the proximal end 210 of the tibia 200 to surround a portion of the tibia 200, and includes a front part 111 and a top part 112.

The front part 111 is a component positioned on the front portion of the proximal end 210 of the tibia 200 to surround a portion of the tibia 200, and includes the abutting surface 111a and the like. The front part 111 may have the cutting member insertion window 12, the fixing holes 13, the mechanical axis indicator 15, the amputation plane guideline 161, and the like formed thereon, as will be described later.

The abutting surface 111a is a component formed on the inner surface of the front part 111 to surround the front portion of the proximal end 210 of the tibia 200, i.e. the abutting surface 111a has the negative shape of the tibia 200 that the abutting surface 111a abuts. The abutting surface 111a is formed on the basis of the 3D data of the tibia 200 of each patient.

The top part 112 is bent and extends from the top end of the front part 111 and is positioned on top of the proximal end 210 of the tibia 200 to surround a portion of the tibia 200. The top part 112 includes the abutting surface 112a and the like. The positioning hole 14 or the like, which will be described later, may be formed on the top part 112.

The abutting surface 112a is a component formed on the inner surface of the top part 112 to surround the upper portion of the proximal end 210 of the tibia 200, i.e. the abutting surface 112a has the negative shape of the abutting tibia 200 that the abutting surface 112a abuts. The abutting surface 112a is formed on the basis of the 3D data of the tibia 200 of each patient.

The cutting member insertion window 12 is a component extending through the front part 111 to accommodate a cutting member (not shown) that is inserted thereinto to form the amputation plane 220. The cutting member insertion window 12 is formed on the basis of the 3D data of the tibia 200 of each patient. The cutting member insertion window 12 has a predetermined shape, and preferably, is oblong-shaped. The cutting member may be implemented as, for example, a surgical saw.

The fixing holes 13 are components extending through the front part 111 at predetermined distances from the cutting member insertion window 12 to accommodate fixing members (not shown) that couple the tibia 200 and the body 11. The distal ends of the fixing members inserted into the fixing holes 13 penetrate into the tibia 200 to firmly fix the tibia 200 and the body 11. The fixing holes 13 include first fixing holes 13a extending from the front surface in the front-rear direction and a second fixing hole 13b extending obliquely from a side surface.

The positioning hole 14 is a component extending through the top part 112 to accommodate and guide a post recess-forming member 2 that is used when forming the post recess 231, which accommodates the post 420 of the tibial element 400, in the tibia 200. The positioning hole 14 is formed on the basis of the 3D data of the tibia 200 of each patient.

The post recess-forming member 2 inserted into the positioning hole 14 penetrates into the tibia 200, thereby forming the post recess 231 in the tibia 200. The post recess-forming member 2 may be implemented as, for example, a drill that is commonly used to form a hole in a bone. Since the positioning hole 14 is formed on the basis of the 3D data of the tibia 200, when the body 11 is coupled in position to the damaged tibia 200, the post recess-forming member 2 can be inserted into the positioning hole 14 and then can be rotated to accurately form the post recess 231 as intended. In the related art, the amputation plane 220 is formed using the patient-customized tibial surgical instrument 1, the patient-customized surgical instrument 1 is removed, the position of the post recess 231 to be formed is determined, and then the post recess 231 is formed using the post recess-forming member 2. According to the patient-customized tibial surgical instrument 1, it is not required to determine the position in which the post recess 231 is to be formed since the positioning hole 14 formed on the basis of the 3D data of the tibia 200 of each patient guides the post recess-forming member 2. It is thereby possible to easily form the surgical site.

The mechanical axis indicator 15 is a component formed in one portion of the body 11 to provide an indication with which the mechanical axis 600 (of the tibia 200) of a lower limb can be visually identified. The mechanical axis indicator 15 includes a connector 151, the indicator bar 152, and the like. The mechanical axis indicator 15 is formed on the basis of the 3D data of the tibia 200 of each patient. Reference will be made to the mechanical axis 600 of the lower limb before the mechanical axis indicator 15 is described. As illustrated in FIG. 7, the mechanical axis 600 refers to a mechanical axis of the lower limb (the femur 100 or the tibia 200). Since the mechanical axis 600 is an index commonly used in the orthopedics, detailed descriptions thereof will be omitted.

The connector 151 is a component protruding from the front surface of the front part 111 to fix the indicator bar 152 to the body 11. The connector 151 includes a coupling hole 151a or the like, the coupling hole 151a extending in the top-bottom direction to accommodate the indicator bar 152. The connector 151 protrudes forward to facilitate the insertion of the indicator bar 152. The coupling hole 151a is elongated in the longitudinal direction, such that the indicator bar 152 can be reliably guided thereby.

The indicator bar 152 is a component inserted into the coupling hole 151a of the connector 151 to be fixed to the body 11, such that the position of the mechanical axis 600 of the tibia 200 can be identified thereby. Although the indicator bar 152 has a predetermined shape, it is preferable that the indicator bar 152 has the shape of a bar, the cross-section of which is one selected from among a circle, a quadrangle, a hexagon, and the like. Since the mechanical axis indicator 15 is formed on the basis of the 3D data of the tibia 200, when the body 11 is coupled in position to the damaged tibia 200, the indicator bar 152 of the mechanical axis indicator 15 is aligned with the mechanical axis 600 of the tibia 200. That is, when the body 11 is coupled to the proximal end 210 of the tibia 200 and the indicator bar 152 is inserted into the coupling hole 151a, such that the leading end of the indicator bar 152 is directed toward the intercondylar eminence a of the tibial plateau and the distal end of the indicator bar 152 is directed toward the talocrural joint b, the indicator bar 152 is positioned on the mechanical axis 600 of the tibia 200, as illustrated in FIG. 8. Thus, it is possible to align the indicator bar 152 with the mechanical axis 600 by adjusting the position in which the body 11 is coupled to the tibia 200, whereby the body 11 is placed in a set position with respect to the tibia 200. The amputation plane 220 of the tibia 200 is oriented perpendicular to the mechanical axis 600 such that arthroplasty causes no problem in the walking of the patient. The patient-customized surgical instrument can bring the body 11 to the set position on the tibia 200 using the mechanical axis indicator 15 such that the position of the body 11 matches the mechanical axis 600 of the tibia 200. It is thereby possible to accurately and easily form the amputation plane 220 of the tibia 200.

The indicator 16 is a component formed on one surface of the body 11 to allow the index of the tibia 200 used when forming the surgical site to be visually identified. The indicator 16 includes the amputation plane guideline 161 or the like. The indicator 16 is formed on the basis of the 3D data of the tibia 200 of each patient.

The amputation plane guideline 161 is a component formed on a side surface of the front part 111 in the front-rear direction to allow the position of the amputation plane 220, which will be formed on the tibia 200, to be identified. The amputation plane guideline 161 is formed on the basis of the 3D data of the tibia 200 of each patient. The body 11 is placed in the set position on the proximal end 210 of the tibia 200 using the fixing member, the cutting member is inserted into the cutting member insertion window 12, and the tibia 200 is cut along the amputation plane guideline 161 using the cutting member, whereby the amputation plane 220 of the tibia 200 is accurately formed. The amputation plane 220 is formed perpendicular to the indicator bar 152, i.e. the mechanical axis 600 of the lower limb. Since the body 11 is formed of a synthetic resin, such as polyethylene, the body 11 may be easily damaged by the cutting member. Thus, the cutting member insertion window 12 is formed significantly larger than the cutting member such that the body 11 is not damaged by the cutting member when the amputation plane 220 is being formed using the cutting member. Since the amputation plane guideline 161 guides the position of the cutting member in the patient-customized surgical instrument, it is possible to accurately form the amputation plane 220 such that the body 11 is not damaged.

The keel recess-forming member 3 is a component to be coupled to amputation plane 220 of the tibia 200 to form the keel recesses 232 after the amputation plane 220 and the post recess 231 of the surgical site are formed using the patient-customized tibial surgical instrument 1. The keel recess-forming member 3 includes a casing 31, a support plate 32, a keel recess-forming part 33, fixing pins 34, and the like.

The casing 31 is a component, the distal end of which is inserted into the post recess 231. The casing 31 accommodates the keel recess-forming part 33 that can move up and down. The casing 31 has blade holes 311. Although the casing 31 has a predetermined shape, it is preferable that the casing 31 has the shape of a cylinder, the hollow space of which is open in the top-bottom direction.

The blade holes 311 are components extending upward predetermined lengths from the outer peripheries of the distal end of the casing 31. Blades 332 of the keel recess-forming part 33 protrude outwards through the blade holes 311.

The support plate 32 is a component coupled to the outer periphery of the bottom of the casing 31 to abut the amputation plane 220 of the tibia 200. The support plate 32 includes guide holes 321 and pin holes 322 extending therethrough in the top-bottom direction. The guide holes 321 function as passages through which the blades 332 move up and down. The pin holes 322 are formed at predetermined distances from the guide holes 321, such that the fixing pins 34 are fitted thereinto.

The keel recess-forming part 33 includes a lift bar 331 and the blades 332. The lift bar 331 is positioned within the casing 31 to be movable up and down. The blades 332 are formed on the lower peripheries of the lift bar 331 to protrude outside of the casing 31 through the blade holes 311. The shapes of the blades 332 correspond to those of the keel recesses 232. The blades 332 form the keel recesses 232 in the tibia 200.

The lift bar 331 is a component positioned within the casing 31 to be movable up and down. The lift bar 331 includes a first lift bar 331a and a second lift bar 331b screw-engaged with each other. A stopper head 331c is formed on the top end of the first lift bar 331a to limit the depth to which the lift bar 331 moves downwards.

The blades 332 protrude from the peripheries of the second lift bar 331 to extend outside of the casing 31 through the blade holes 311. The blades 332 move up and down along with the lift bar 311 to form the keel recesses 232 in the tibia 200.

In conjunction with FIGS. 1 to 12, reference will be made to a method of forming a surgical site in the tibia 200 using the surgical module configured as described above. As illustrated in FIG. 8, the body 11 is positioned on the proximal end 210 of the tibia 200. The indicator bar 152 is inserted into the coupling hole 151a, with the leading end thereof being directed toward the intercondylar eminence a of the tibial plateau, and the distal end thereof being directed toward the talocrural joint b, such that the indicator bar 152 is aligned with the mechanical axis 600 of the tibia 200. Then, the body 11 is fixed to the proximal end 210 of the tibia 200, and the indicator bar 152 is removed. Afterwards, as illustrated in FIG. 11, the post recess-forming member 2 is inserted into the positioning hole 14 to form the post recess 231 in the tibia 200, and the cutting member is inserted into the cutting member insertion window 12 to cut the tibia 200 along the amputation plane guideline 161, thereby forming the amputation plane 220 perpendicular to the mechanical axis 600 of the tibia 200. Sequentially, the cutting member, the patient-customized tibial surgical instrument 1, and cut bone fragments are removed from the tibia 200. The keel recess-forming member 3 is attached to the tibia 200 by coupling the support plate 32 to the amputation plane 220. Afterwards, as illustrated in FIG. 12, the lift bar 331 is moved downwards by pressing the distal end thereof, so that the blades 332 move downward to form the keel recesses 232. After the keel recesses 232 are formed, the keel recess-forming member 3 and cut bone fragments are removed, thereby forming the surgical site on the tibia 200, as illustrated in FIG. 3.

Although the several embodiments of the present invention have been disclosed for illustrative purposes, those skilled in the art will appreciate that various modifications, additions and substitutions are possible, without departing from the scope and spirit of the present invention as disclosed in the accompanying claims.

The invention claimed is:

1. A patient-customized tibial surgical instrument used in formation of a surgical site such that a tibial element comprising a post protruding from a flat end is able to be transplanted on a tibia, the patient-customized tibial surgical instrument comprising:
    a body comprising: a front part configured to be positioned on a front portion of a proximal end of a tibia and having an abutting surface configured to abut and surround the front portion of the tibia, the abutting surface of the front part having a custom negative shape of the abutting tibia; and a top part bent and extending from a top end of the front part and configured to be positioned on top of the proximal end of the tibia, and the top part having an abutting surface configured to abut and surround a portion of the tibia, the abutting surface of the top part and the abutting surface of the front part both being fabricated and customized based on three-dimensional data of the tibia before the abutting tibia is cut;
    a cutting member insertion window extending through a portion of the front part of the body, the cutting member insertion window configured to accommodate a cutting member inserted thereinto to form an amputation plane of the tibia during use; and
    a customized positioning hole positioned on the body based on the three-dimensional data of the tibia so as to extend through the top part of the body and between a medial and lateral plateau of the tibia, wherein the positioning hole is completely encircled by the body and is configured to accommodate and guide a post recess-forming member used to form a post recess between the medial and lateral plateaus of the tibia during use so that the post recess is formed at a location based on the three-dimensional data of the tibia;
    a mechanical axis indicator disposed on the body to provide an indication with which a mechanical axis of the tibia is visually identifiable, wherein the mechanical axis indicator comprises:
        a connector protruding from the front part of the body to fix an indicator bar to the body; and
        the indicator bar removably coupled to the connector to be fixed to the body and allowing a position of the mechanical axis to be identified, when one end of the indicator bar is directed to an intercondylar eminence of a tibial plateau during use and the other end of the indicator bar is directed to a talocrural joint during use, the indicator bar is aligned with the mechanical axis of the tibia during use,
wherein the front part of the body includes:
an upper portion disposed on a side of the cutting member insertion window toward the top part; and
a lower portion disposed on a side of the cutting member insertion window opposite the upper portion, the connector protruding from the upper portion of the front part of the body.

2. The patient-customized tibial surgical instrument according to claim 1, further comprising an amputation plane guideline disposed on a portion of the body to provide an indication with which a position of the amputation plane to be formed on the tibia is identifiable.

3. The patient-customized tibial surgical instrument according to claim 2, wherein the amputation plane guideline outwardly projects from the front part of the body.

4. The patient-customized tibial surgical instrument according to claim 2, wherein the amputation plane guideline is disposed on the front part and is laterally aligned with the cutting member insertion window when the customized positioning hole is vertically disposed.

5. The patient-customized tibial surgical instrument according to claim 4, wherein the amputation plane guideline and the cutting member insertion window are disposed within a common plane.

6. The patient-customized tibial surgical instrument according to claim 4, wherein the amputation plane guideline is positioned based on the three-dimensional data of the tibia.

7. A surgical module using a patient-customized tibial surgical instrument used in formation of a surgical site such that a tibial element is able to be transplanted on a tibia, the surgical module comprising:
the patient-customized tibial surgical instrument described in claim 1 and configured to be coupled with a proximal end of the tibia to be used in formation of an amputation plane and a post recess of the surgical site; and
a keel recess-forming member, wherein, after the amputation plane and the post recess of the surgical site are formed using the patient-customized tibial surgical instrument, the keel recess-forming member is configured to be coupled to the amputation plane to form a keel recess.

8. The surgical module according to claim 7, wherein the keel recess-forming member comprises:
a casing having one end inserted into the post recess to accommodate a keel recess-forming part that is movable up and down;
a support plate coupled to an outer periphery of the casing to abut the amputation plane of the tibia; and
the keel recess-forming part comprising a lift bar positioned within the casing to be movable up and down and a blade disposed on a lower periphery of the lift bar to protrude outside of the casing through a blade hole, wherein the blade is movable up and down along with the lift bar to form the keel recess in the tibia.

9. The surgical module according to claim 8, wherein the support plate has a guide hole extending therethrough in a top-bottom direction, the guide hole functions as a passage through which the blade moves up and down.

10. The surgical module according to claim 8, wherein a stopper head is disposed on a top end of the lift bar to limit a depth to which the lift bar moves downwards.

11. The surgical instrument as recited in claim 1, wherein the top part is integrally formed as a single unitary member with the front part.

12. The patient-customized tibial surgical instrument according to claim 1, wherein the body is comprised of a synthetic resin.

13. The patient-customized tibial surgical instrument according to claim 1, wherein the mechanical axis indicator is positioned so that when the customized positioning hole is vertically aligned, a horizontal plane passing through the cutting member insertion window intersects with the indicator bar removably coupled to the connector.

14. The patient-customized tibial surgical instrument according to claim 1, wherein the cutting member insertion window is formed based on the three-dimensional data of the tibia.

15. The patient-customized tibial surgical instrument according to claim 3, wherein the mechanical axis indicator is formed based on the three-dimensional data of the tibia.

16. A surgical instrument used in formation of a surgical site on a proximal end of a tibia such that after the surgical instrument is used, a tibial element comprising a flat end and a post protruding from the flat end is able to be transplanted onto the surgical site, the surgical instrument comprising:
a body comprising:
a front part having a first abutting surface configured to be positioned on a proximal front surface of the tibia during use, the first abutting surface of the front part being fabricated and customized based on three-dimensional data of the tibia before the tibia is cut;
a top part extending from the front part and having a second abutting surface configured to be positioned on a proximal top surface of the tibia during use, the second abutting surface of the top part being fabricated and customized based on the three-dimensional data of the tibia before the tibia is cut;
an insertion window extending through the front part of the body; and
a positioning hole extending through the top part of the body, the positioning hole being completely encircled by the body, wherein the positioning hole is configured to accommodate and guide a post recess-forming member used to form a post recess, the positioning hole being positioned on the body based on the three-dimensional data of the tibia so that the post recess is formed at a location based on the three-dimensional data of the tibia, wherein the body is configured so that when secured to the proximal end of the tibia during use, the positioning hole is positioned between a medial and lateral plateau of the tibia; and
a mechanical axis indicator disposed on the body to provide an indication with which a mechanical axis of the tibia is visually identifiable, wherein the mechanical axis indicator comprises:
a connector protruding from the front part of the body to fix an indicator bar to the body; and
the indicator bar removably coupled to the connector to be fixed to the body and allowing a position of the mechanical axis to be identified, when one end of the indicator bar is directed to an intercondylar eminence of a tibial plateau during use and the other end of the indicator bar is directed to a talocrural joint during use, the indicator bar is aligned with the mechanical axis of the tibia during use, wherein the front part of the body includes:
- an upper portion disposed on a side of the insertion window toward the top part; and
- a lower portion disposed on a side of the insertion window opposite the upper portion, the connector protruding from the upper portion of the front part of the body.

17. The surgical instrument as recited in claim 16, wherein the top part is integrally formed as a single unitary member with the front part.

* * * * *